United States Patent [19]
van den Haak

[11] Patent Number: 5,573,512
[45] Date of Patent: Nov. 12, 1996

[54] INFUSION OR TRANSFUSION NEEDLE ASSEMBLY

[75] Inventor: Abraham van den Haak, Eesergroen, Netherlands

[73] Assignee: Advanced Protective Injection Systems B.V., Eesergroen, Netherlands

[21] Appl. No.: 39,288

[22] PCT Filed: Aug. 2, 1991

[86] PCT No.: PCT/NL91/00144

§ 371 Date: Apr. 19, 1993

§ 102(e) Date: Apr. 19, 1993

[87] PCT Pub. No.: WO92/04073

PCT Pub. Date: Mar. 19, 1992

[30] Foreign Application Priority Data

Sep. 5, 1990 [NL] Netherlands ............... 9001958
Nov. 22, 1990 [NL] Netherlands ............... 9002552

[51] Int. Cl.$^6$ ............................................. A61M 5/00
[52] U.S. Cl. ........................ 604/171; 604/110; 604/198
[58] Field of Search ........................ 604/110, 187, 604/192, 198, 263, 171

[56] References Cited

U.S. PATENT DOCUMENTS

| | | |
|---|---|---|
| 4,160,450 | 7/1979 | Doherty . |
| 4,804,372 | 2/1989 | Laico et al. . |
| 4,894,055 | 1/1990 | Sudnak ................................ 604/198 |
| 4,917,669 | 4/1990 | Bonaldo . |
| 4,935,012 | 6/1990 | Magre et al. ......................... 604/192 |
| 4,985,021 | 1/1991 | Straw et al. ......................... 604/198 |
| 4,998,924 | 3/1991 | Ranford ................................ 604/798 |
| 5,070,884 | 12/1991 | Columbus et al. .................. 128/760 |
| 5,088,982 | 2/1992 | Ryan .................................... 604/110 |

FOREIGN PATENT DOCUMENTS

| | | |
|---|---|---|
| 0369972 | 5/1990 | European Pat. Off. . |
| 8803216 | 9/1988 | Germany . |
| 90/03196 | 4/1990 | WIPO . |

Primary Examiner—Corrine M. McDermott
Attorney, Agent, or Firm—Bell, Seltzer, Park & Gibson, P.A.

[57] ABSTRACT

An infusion or transfusion needle assembly includes a hollow needle fixed to a needle holder. The needle holder is surrounded by a sheath such that the sheath and the needle holder are axially slidable relative to one another. Releasable detent locking means are provided between the needle holder and the sheath to positively prevent axial movement of the needle holder and needle relative to the sheath, thereby locking the needle in an extended position for insertion into the skin of a patient. Unlocking means are provided for releasing the releasable detent locking means, thereby permitting axial movement of the needle holder and needle relative to the sheath so that the needle is movable from the extended position to a fully retracted position within the sheath. Once the needle is fully retracted, permanent detent locking means become operative to positively and permanently maintain the needle in the retracted position.

12 Claims, 6 Drawing Sheets

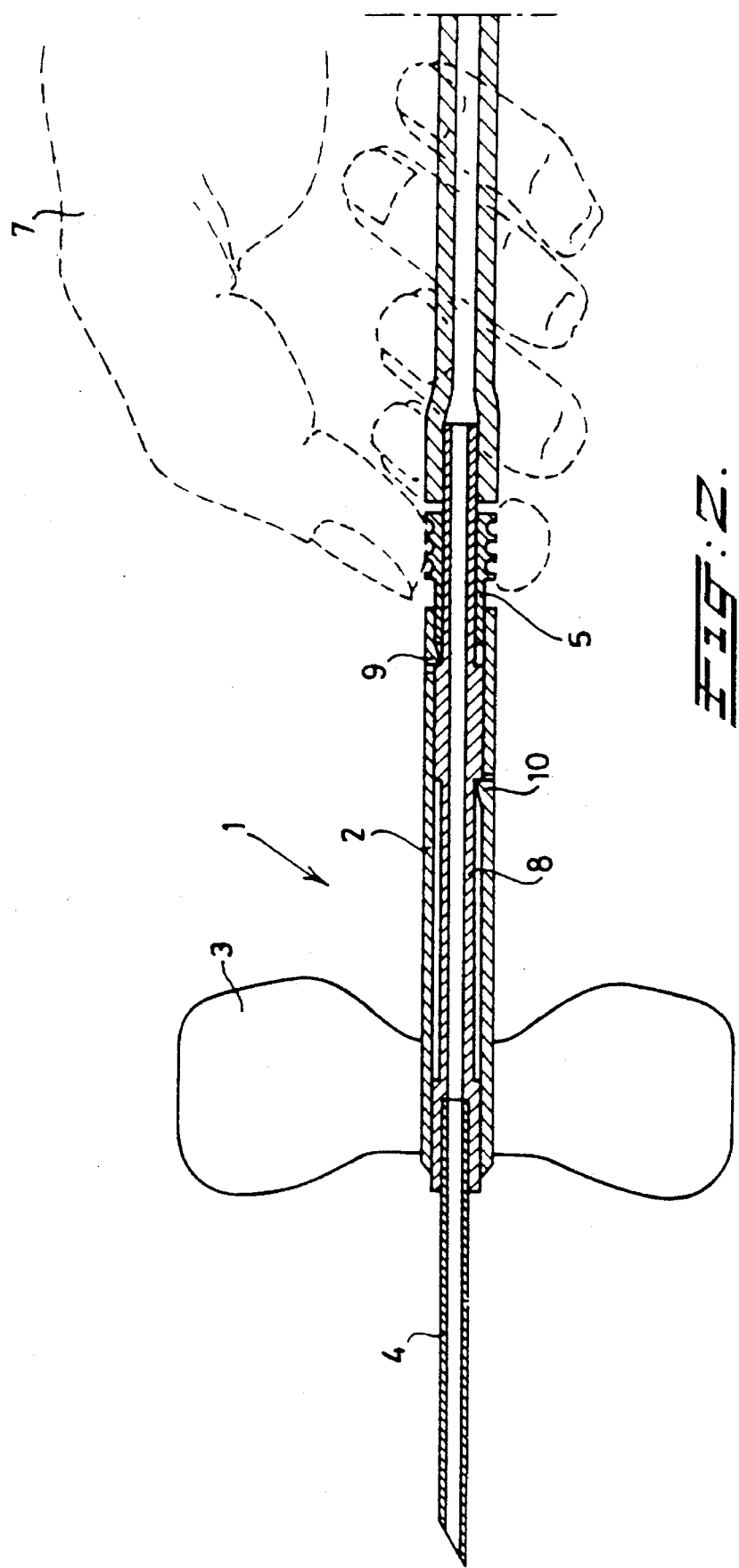

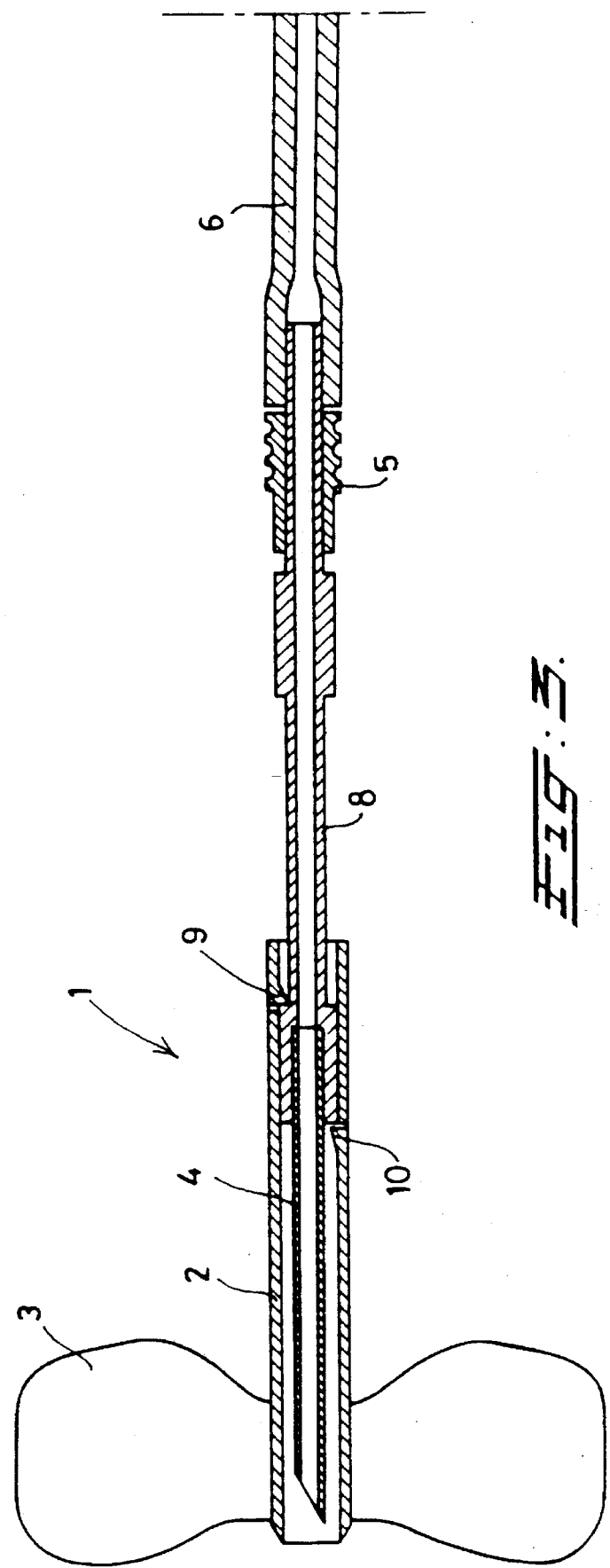

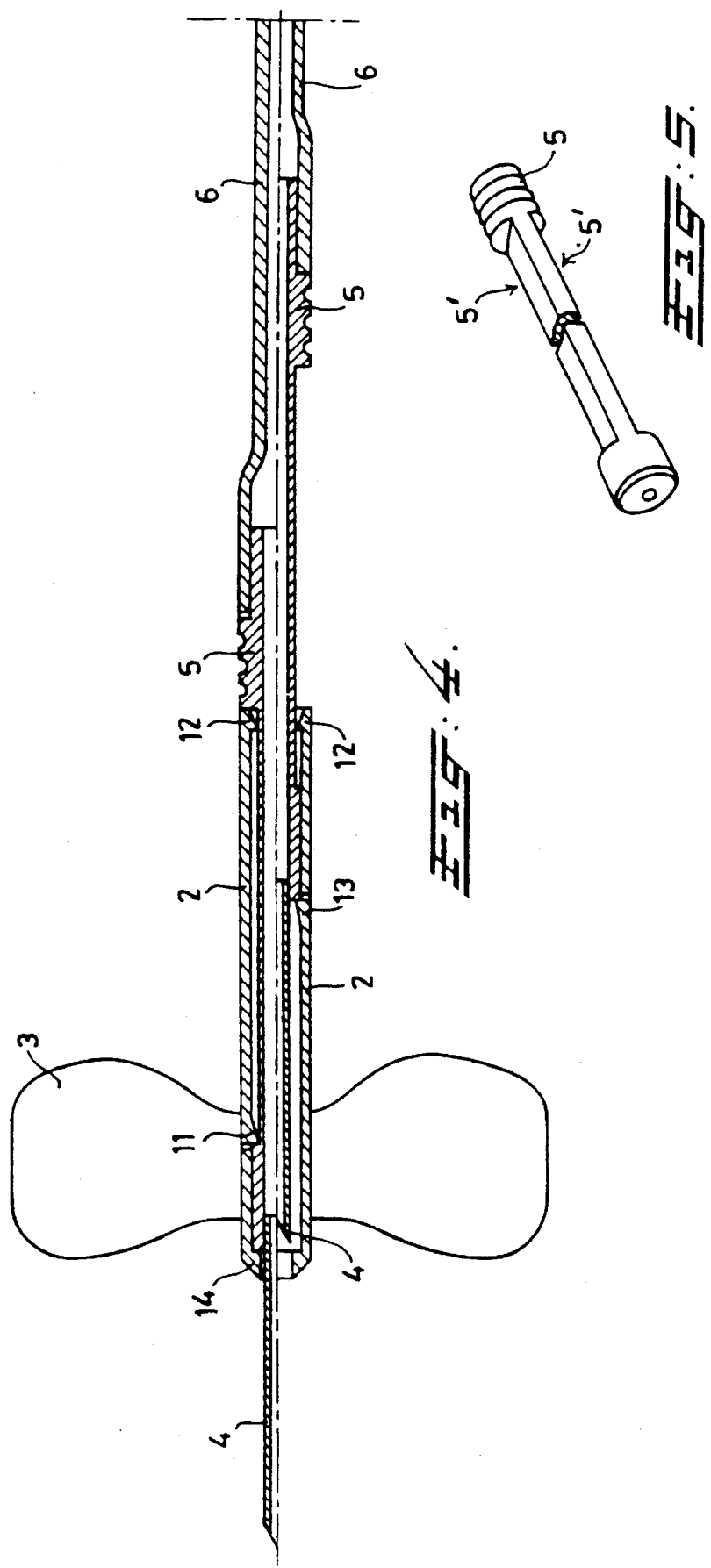

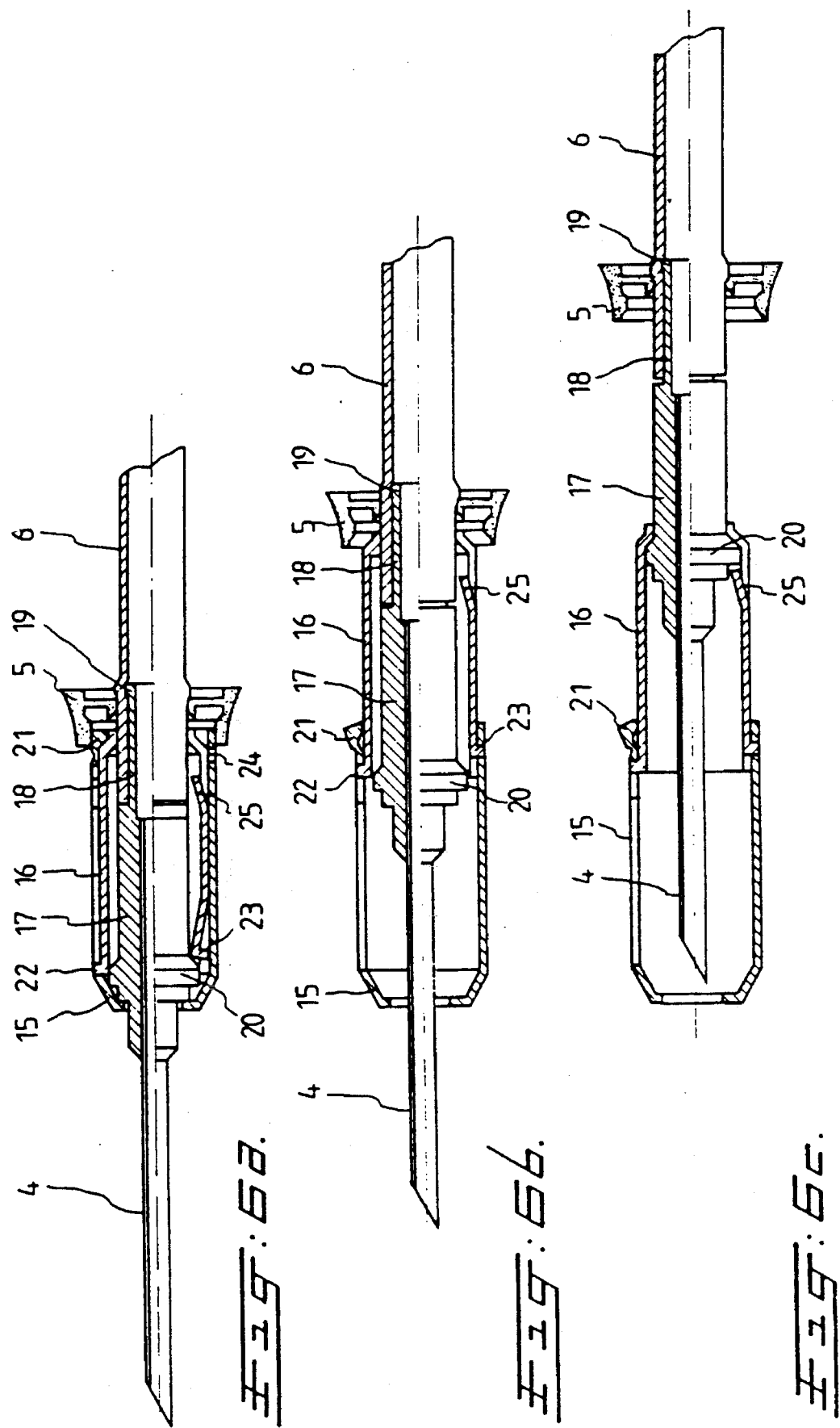

INFUSION OR TRANSFUSION NEEDLE ASSEMBLY

The present invention relates to an infusion or transfusion needle assembly, at least comprising a hollow needle fixed in a needle holder, which needle holder is or can be connected to a connecting hose.

Such a needle assembly or cannula is known from, for example, DE-U-88 12 099. This publication describes a cannula for vessel puncture, in particular for blood treatment outside the body, for example dialysis or plasmaphoresis. In order to ensure that the needle is sterile, the needle is situated in a protective cap which is removed before use. After use of the cannula, the needle can be inserted into the protective cap at the other side, and is pushed through a membrane, this being in order to prevent injury from the needle. Since a patient on whom the cannula is used could have other, possibly transmittable diseases apart from the condition treated with the cannula, injury from a used needle could have extremely serious consequences.

The major disadvantage of this cannula is that, despite the use of the protective cap as a needle protection after use, there is still a risk of injury. It is in fact always necessary to exert some force in order to pierce the membrane, in the course of which the needle could shoot out. The needle could also miss the cap and accidentally be pushed into the hand holding the cap. The cap can also easily be lost, due to the fact that most treatments with a cannula last a relatively long time (a dialysis treatment generally takes about six hours). This means that the cannula will then be thrown away with an unprotected needle, thus producing the risk of injury.

Finally, the cannula according to the publication also has the disadvantage that the wound formed by the needle is often damaged during removal of the cannula, due to the fact that the plaster or other fixing means by which the cannula is fixed to the skin has to be removed first of all before the needle can be removed from the skin. The removal of the plaster results in the needle being pulled slightly askew in the blood vessel. This pulling askew can also be painful for a patient in whom the cannula is inserted.

The object of the present invention is to eliminate the above-mentioned disadvantages, and to this end the invention is characterised in that the needle holder is slidable accommodated in a sheath, and in that locking means are present between the needle holder and the sheath, said locking means being designed in such a way that after unlocking of the needle holder the needle can be pushed fully into the sheath and locked therein.

This makes it possible to draw the needle into the sheath after use of the assembly, something which can be performed with one hand or with both hands. It is important here that the forces used for displacement of the needle are always directed in the longitudinal direction of the needle, but never towards the pointed end thereof, which minimises the risk of the needle shooting out and thereby causing injuries.

The problem of the needle being pulled askew in the blood vessel during removal of the assembly is also eliminated, through the fact that the needle is pulled out of the blood vessel into the sheath before the plaster is removed. A cotton wool plug or something similar is generally held on the wound with one hand during this operation. The needle can then be pulled back into the sheath with the other hand, and the plaster can be removed without any adverse or painful effects for the wound which has been formed by the needle. After these operations the needle is pushed into the sheath and locked, and any risk of injury afterwards is virtually ruled out. Moreover, the assembly cannot be re-used, and can be thrown away without the need for fitting a protective cap or the like.

Advantageous embodiments of the infusion needle assembly according to the invention are described in the sub-claims.

The invention will be explained in greater detail below with reference to the appended drawing; in which:

FIG. 2 shows the infusion needle assembly according to FIG. 1, in cross-section;

FIG. 3 shows the infusion needle assembly according to FIG. 2, in the position in which the needle is withdrawn into the sheath;

FIG. 4 shows an infusion needle assembly according to another embodiment of the invention, in which the top cross-section shows the normal position and the bottom cross-section shows the position with retracted needle;

FIG. 5 shows a perspective view of the unlocking element shown in FIG. 4;

FIGS. 6a–6c show views, partially in cross-section, of a particular embodiment of an infusion needle assembly according to the invention in different positions.

Figure 1:
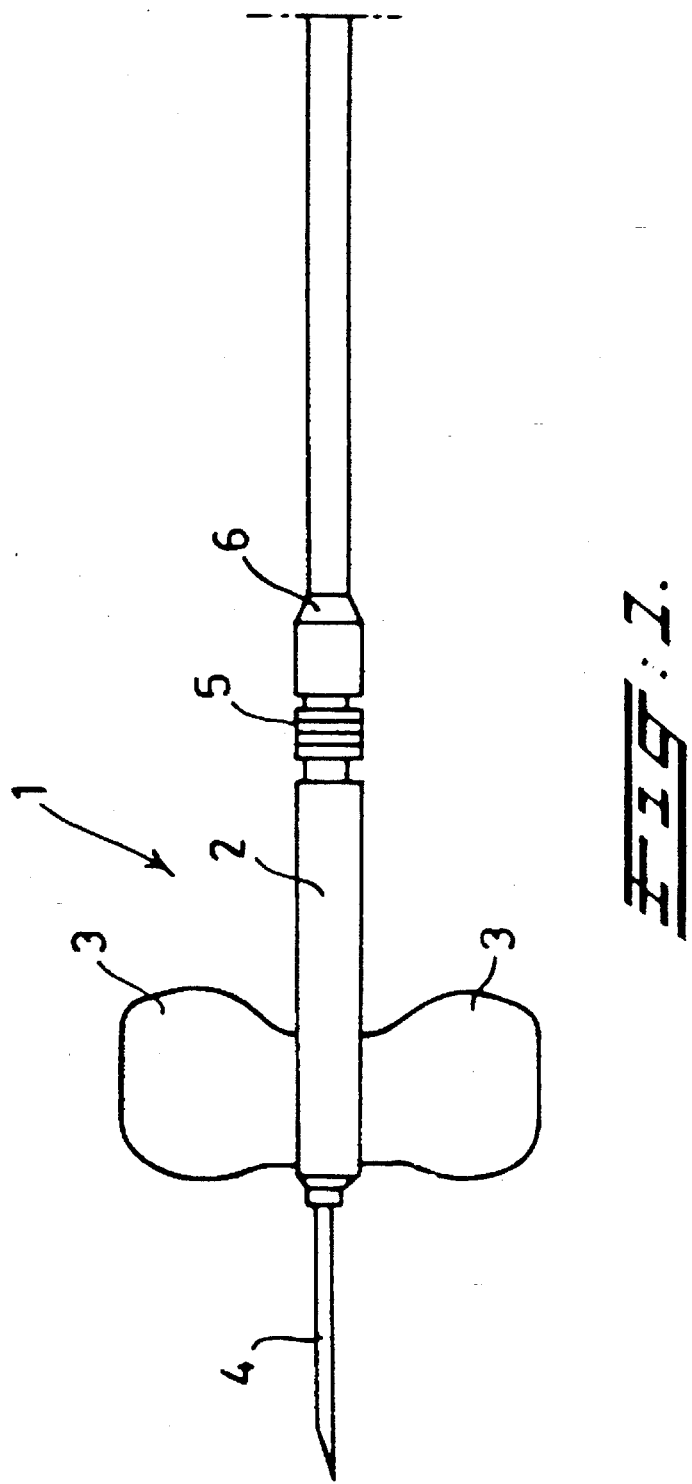
FIG. 1 shows an infusion needle assembly according to the invention.

FIG. 1 shows an infusion needle assembly 1 according to the invention, in which a sheath is indicated by 2. Reference number 3 indicates two holding wings which serve for holding the needle assembly 1 during insertion of the needle through the skin, and for sticking the assembly on the skin, for example by means of a plaster or the like. A hose 6 for supplying and discharging treatment fluid is shown. A part of an unlocking element 5 can be seen between the hose 6 and the sheath 2.

FIG. 2 shows a cross-section of the infusion needle assembly according to FIG. 1. The needle holder 8 connecting the needle 4 to the hose 6 can be seen in this cross-section. The needle holder is held in place in the sheath 2 by the presence of two projections 9 and 10. The unlocking element 5 is slidable along the needle holder 8 and can be pushed between the thumb and forefinger of one hand 5 into the sheath 2. The cylindrical part of unlocking element 5 is capable of lifting projection 9, as a result of which it is possible to move the needle holder 8 into the sheath 2, so that after use of the infusion assembly 1, the needle 4 can be drawn fully into the sheath 2, for example using the other fingers of the same hand.

This retracted position of the infusion needle assembly 1 according to FIGS. 1 and 2 is shown in FIG. 3. In this position the assembly can be thrown away without the risk of injury. The actions needed for retracting of the needle are very simple and can be performed with one hand. This means that it has become virtually impossible to injure someone accidentally with the needle during these actions.

It will be appreciated that the unlocking element 5 can be designed in such a way that it lifts the locking elements, in this case projections 9 and 10, when it is being pulled out of the sheath 2.

FIG. 4 shows an infusion needle assembly according to the invention in which a different locking mechanism is used. The unlocking element 5 serves as a needle holder at the same time. In this figure the extended position of the assembly is shown in the top half, and the retracted position in the bottom half. The unlocking element 5 (also needle holder) is held in the sheath between projection 11 and the front side 14 of the sheath. As shown in FIG. 5, the element 5 has recesses 5', but these have a closed bottom, in order to permit the passage of liquid such as blood or the like through the element 5. Projection 11 is lifted by turning the element 5 in the top half of FIG. 4 a quarter turn, and the element can be moved in the sheath 2 and the needle 4 pulled into it. This retracted position is shown in the bottom half of FIG. 4. After passing projection 13, the element 5 is held fixed through the presence of projections 12 and 13.

A special embodiment of the needle assembly according to the invention is shown in FIGS. 6a–6c, in which the sheath is composed of two sheaths 15 and 16 which are slidable relative to each other. FIG. 6a shows the extended position of the needle, FIG. 6b an intermediate position, and FIG. 6c the retracted position of the needle. Reference number 4 again shows the needle, and reference number 6 the connecting hose. The needle 4 is situated in a needle base 17, which is provided with an insertion end 18 with an annular thickened part 19 at the end thereof. The connecting hose 6, which is fixed, for example by means of adhesive, is pushed over this insertion end 18. The unlocking element 5—which in FIGS. 6a and 6b is situated between the end of the sheaths 15, 16 and the annular thickened part 19 with the connecting hose 6 pushed over it—is also situated over the insertion end 18 provided with the connecting hose 6 pushed on to it.

As shown clearly in FIG. 6a, the insertion end 18 with the connecting hose 6 pushed over it is situated inside the sheaths 15, 16, which produces a considerable saving in the length of the infusion needle assembly. This fixing of the connecting hose to the needle holder can, of course, also be used for the embodiments discussed earlier.

The needle holder 17 is provided with a collar 20, and the outer sheath 15 is provided with a locking projection 21, which can interact with the unlocking element 5.

For the sake of simplicity, no holding wings are shown in FIGS. 6a–6c.

If after use, while the cannula is still fixed by means of a plaster or the like, the unlocking element 5 is pulled in the direction of the hose 6, the projection 21 of the outer sheath 15 is lifted, and the inner sheath 16 with the needle holder—and thus the needle—in it can be shifted relative to the outer sheath 15 (see FIG. 6b). When the projection 22 of the inner sheath 16 strikes against the rear side of the projection 21, the pretensioned lip projection 23 snaps at the same moment into a recess 24, as a result of which the sheaths 15 and 16 are fixed relative to each other. If the movement of the unlocking element 5 is continued, the needle holder 17 with the needle 4 fixed to it is moved relative to the two sheaths 15, 16, and the position shown in FIG. 6c is finally obtained, with the collar 20 clicking behind a locking projection 25. The needle holder 17 is thereby locked with the needle 4 relative to the two sheaths 15, 16, and re-use of the needle is thus prevented.

An extremely important advantage of the embodiment shown in FIGS. 6a–6c is that the length of the sheath is considerably reduced (more than half). This has the advantage that the force moment exerted on the needle by the hose, which is generally bent back in the direction of the needle 4, is considerably reduced, and the risk of injury when the needle is in a blood vessel and the hose is pulled is reduced.

Figure 7:
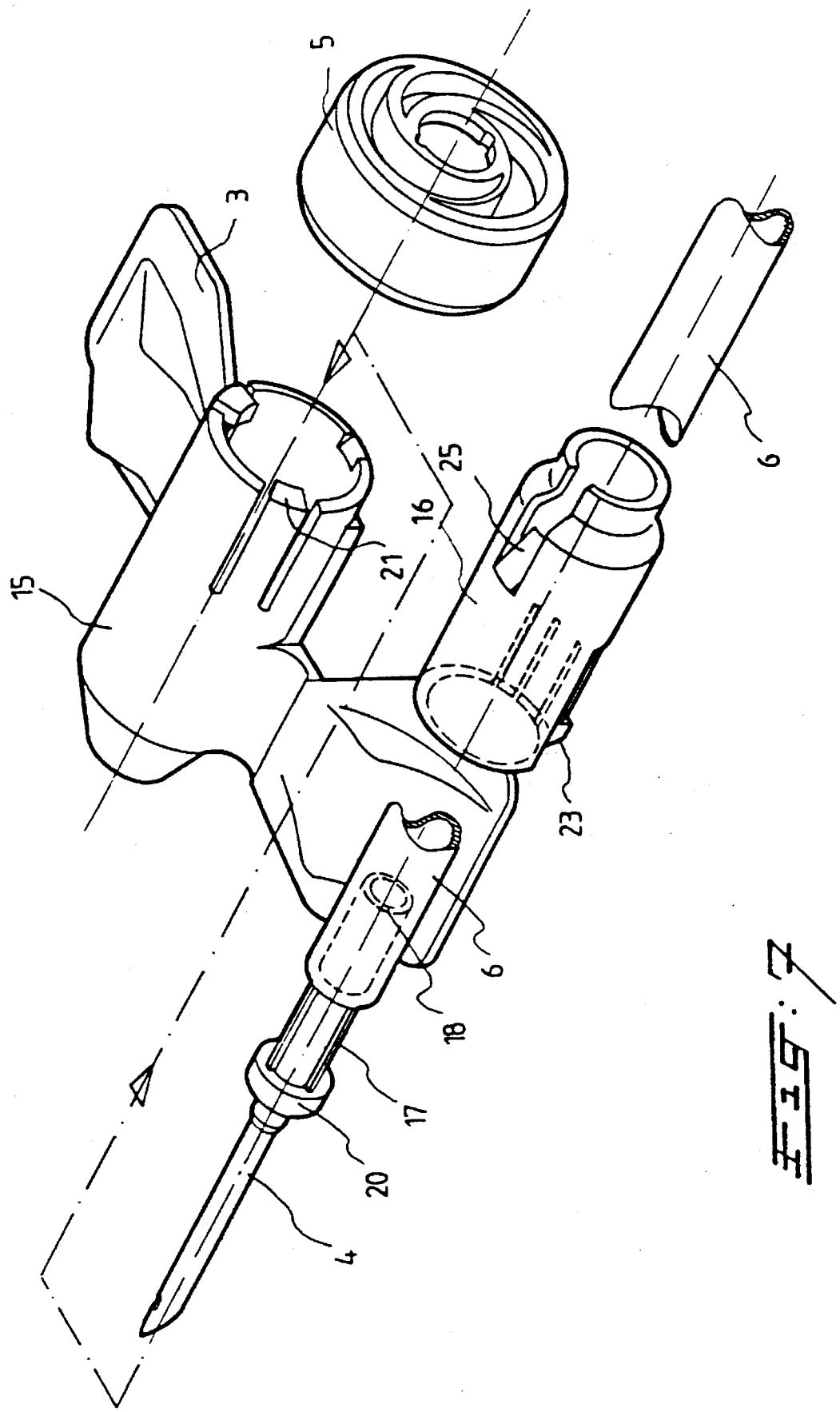
FIG. 7 shows a simplified perspective view of the needle assembly shown in FIGS. 6a–6c, taken apart.

FIG. 7 shows schematically a perspective view of the needle assembly according to FIGS. 6a–6c, taken apart. The dashed and dotted line with the arrows indicates the direction in which the assembly can be fitted. For the sake of simplicity, not all parts are shown in FIG. 7, but the needle assembly according to FIGS. 6a–6c is shown only schematically.

It will be clear that, as a result of the above description, many other embodiments are obvious to the expert, for example providing the sheath in the form of more than two mutually slidable sheaths, or designing the locking means in a different way.

I claim:

1. An infusion or transfusion needle assembly comprising:

a hollow needle;

a tubular needle holder having a first end connected to said needle and a second end adapted to be connected to a hose;

a tubular sheath coaxially surrounding at least a portion of said needle holder so as to be axially slidable relative to said needle holder and needle between an extended position wherein the needle extends from the sheath and is ready for use, and a retracted position wherein the needle is protectively covered by the sheath;

releasable detent locking means mounted on at least one of said needle holder and said sheath for releasably locking said sheath in said extended position and preventing axial movement of said sheath from said extended position to said retracted position;

an unlocking element mounted on at least one of said needle holder and said sheath and selectively moveable into or out of engagement with said releasable detent locking means for releasing said releasable detent locking means to permit axial movement of said sheath from said extended position to said retracted position; and permanent detent locking means mounted on at least one of said needle holder and said sheath for permanently locking said sheath in said retracted position upon said sheath being moved from said extended position to said retracted position.

2. The needle assembly according to claim 1 wherein:

said needle holder includes a first radially raised section and a second radially raised section which is axially spaced from said first radially raised section, said first and second radially raised sections each defining a pair of axially spaced apart and oppositely facing shoulders;

said releasable detent locking means comprises a pair of axially spaced apart detents on the inside diameter of said sheath to engage respectively with said pair of axially spaced shoulders of said first radially raised section in said extended position; and said permanent detent locking means comprises said pair of detents to engage respectively with said pair of axially spaced shoulders of said second radially raised section in said retracted position.

3. The needle assembly according to claim 2 wherein said unlocking element comprises a separate sleeve coaxially mounted upon said needle holder for movement between an inoperative position and an operative position in contact with one of said pair of detents so as to release its engagement with its associated shoulder.

4. The needle assembly according to claim 1 wherein:

said needle holder includes a radially raised section defining a pair of axially spaced apart and oppositely facing shoulders;

said releasable detent locking means comprises a first pair of axially spaced apart detents on the inside diameter of said sheath to engage respectively with said pair of axially spaced shoulders of said radially raised section in said extended position; and said permanent detent locking means comprises a second pair of detents on the inside diameter of said sheath to engage respectively with said pair of axially spaced shoulders of said radially raised section in said retracted position.

5. The needle assembly according to claim 4 wherein said unlocking element comprises a portion of the axial length of said needle holder adjacent one of said shoulders and which includes a radially recessed circumferential segment and a radially extended circumferential segment, and such that rotation of said needle holder causes said radially extended circumferential segment to be brought into contact with one of said first pair of detents so as to release its engagement with its associated shoulder.

6. The needle assembly accordingly to claim 1 wherein said tubular sheath comprises a plurality of tubular sleeves mounted coaxially with respect to each other and so as to be relatively slidable between an overlapping configuration and a lengthened configuration.

7. The needle assembly according to claim 6 wherein said plurality of tubular sleeve comprises an inner tubular sleeve and an outer tubular sleeve, and with said inner and outer sleeves having forward ends and rearward ends which are respectively aligned in said overlapping configuration.

8. The needle assembly according to claim 7 wherein said needle holder comprises a radially raised section defining a pair of axially spaced apart and oppositely facing shoulders, said releasable detent locking means comprises a first detent on said outer sleeve and a second detent (23) on said inner sleeve for respectively engaging said shoulders, and a third detent (21) on said outer sleeve for engaging the rearward end of said inner sleeve when said sleeves are in said overlapping configuration and said sheath is in said extended position.

9. The needle assembly according to claim 8 wherein said unlocking element comprises a separate sleeve (5) coaxially mounted about said needle holder for movement between an operative position in contact with said third detent so as to hold the same in contact with said rearward end of said inner sleeve, and a release position withdrawn from said third detent so as to permit said third detent to disengage said rearward end of said inner sleeve.

10. The needle assembly according to claim 9 wherein said releasable detent locking means further comprises release means (24) on said outer sleeve for releasing the engagement between said second detent (23) and its associated shoulder upon the sleeves being moved to said lengthened configuration.

11. The needle assembly according to claim 10 wherein said permanent detent locking means comprises a pair of axially spaced apart detents on said inner sleeve adjacent the rearward end thereof for respectively engaging said shoulders when said sheath is in said extended position.

12. The needle assembly according to claim 1 wherein a pair of radially extending wings are positioned on the outside diameter of said sheath.

* * * * *